(12) United States Patent
Morita et al.

(10) Patent No.: US 6,506,305 B2
(45) Date of Patent: Jan. 14, 2003

(54) METHODS OF ISOLATING UREA, UREA COMPOSITIONS AND METHODS FOR PRODUCING THE SAME

(75) Inventors: Minoru Morita, Tokyo (JP); Atsushi Serizawa, Kawagoe (JP); Wataru Motsuchi, Kawagoe (JP); Haruyoshi Yamamoto, Kawagoe (JP); Masanori Kotani, Tokyo (JP); Yoriko Yamane, Takamatsu (JP)

(73) Assignee: Snow Brand Milk Products Co., Ltd., Hokkai-do (JP)

( * ) Notice: Subject to any disclaimer, the term of this patent is extended or adjusted under 35 U.S.C. 154(b) by 0 days.

(21) Appl. No.: 09/866,227

(22) Filed: May 25, 2001

(65) Prior Publication Data

US 2001/0047963 A1 Dec. 6, 2001

Related U.S. Application Data

(62) Division of application No. 09/532,628, filed on Mar. 22, 2000, now abandoned.

(30) Foreign Application Priority Data

Mar. 26, 1999 (JP) .......................................... 11-082721

(51) Int. Cl.$^7$ .......................... B01D 61/02; B01D 61/14
(52) U.S. Cl. ........................ 210/651; 210/650; 210/652
(58) Field of Search ................................ 210/650, 651, 210/652; 564/63, 73

(56) References Cited

U.S. PATENT DOCUMENTS

| 5,085,881 A | 2/1992 | Moeller ...................... 426/491 |
| 5,252,829 A | 10/1993 | Nygaard et al. ............ 250/339 |

FOREIGN PATENT DOCUMENTS

| EP | 0 044 872 A1 | 2/1982 |
| EP | 0 657 466 A1 | 6/1995 |
| GB | 1 536 478 | 12/1978 |
| WO | WO 89/01468 | 2/1989 |

OTHER PUBLICATIONS

CA:123:254895 abs of J Membr Sci by van der Horst 104(3) pp. 205–218 1995.*
CA:70:39274 abs of Ind Eng, Chem Process Des. Develop. by Ohya 8(1) pp. 131–142 1969.*
CA:105:48375 abs of Maku by Ohya 10(6) pp. 371–379 1985.*
CA: 127:4331 abs of Aust J Dairy Technology by Savello et al 52(1) pp. 60–62, 1997.
CA: 86:28775 abs of J Dairy Sci by Huber et al 59(11) pp. 1936–1943, 1976.
CA: 115: 209589 abs of Desalination by Doyen et al 79(2–3) pp. 163–179, 1990.
CA: 108: 74045 abs of SU1073912, Oct.1987.
CA: 97: 22306 abs of J Dairy Res. by Kelly 49(2) pp. 187–196, 1982.
CA: 91: 139005 abs of J Dairy Res by Muir et al 46(2, Proc IDF Symp Phys Chem Milk Proteins) pp. 381–384, 1979.
CA: 105; 189658 abs of Indian J. Dairy Sci by Ramakrishnaiah 38(4) pp. 346–348, 1985.
Zhou, Jianhui, et al., Several engineering equations in the design of reverse osmosis plants, p. 144, col. 1, Chemical Abstract, Desalination vol. 80, No. 1, 1991, pp. 15–30.
Haruhiko Ohya, et al., Reverse–osmosis separation of urea in aqueous solutions using porous cellulose acetate membranes, p. 115, col. 2, Chemical Abstract, Ind. Eng. Chem., Process Des. Develop., vol. 8, No. 1, 1969, pp. 131–142.
Huang R.Y.M., et al., Investigations on nylon 4 membranes: synthesis and transport properties. II. Transport properties of nylon 4 polymer membranes., Chemical Abstracts, Journal of Applies Polymer Science, vol. 29, No. 6, 1981, pp. 1907–1918.
Narola B J et al, Cellulose acetate (CA)–poly(Methlymethacrylate)(PMMA) blend semipermeable membrane. Part IV. for Application of CA–PMMA blend flat membrane for other than brackish water desalination, Chemical Abstracts, Indian Chem. J., vol. 13, No. 11, 1979, pp. 23–24.
Hinmann P V, et al., Composite reverse–osmosis membranes prepared by plasma polymerisation of allylamine. Evaluation of emebrane performance for the treatment of wash water and its components, Chemical Abstract, Journal of Applied Polymer Science, vol. 23, No. 12, 1979, pp. 3651–3656.
Ramachandhran V., et al., Poly(m–phenyleneisophthalamide) membranes for reverse–osmosis separations, Chemical Abstract, Int. J. Polym. Mater., vol. 14, No. 3–4, 1990, pp. 157–163.

* cited by examiner

*Primary Examiner*—Jean F. Vollano
(74) *Attorney, Agent, or Firm*—Knobbe, Martens Olson & Bear LLP

(57) ABSTRACT

Urea is readily isolated and recovered from natural products. Urea can be brought into the permeate side by treating a urea-containing fraction extracted from natural products or sewage containing urea, with a nanofiltration (NF) membrane or reverse osmotic (RO) membrane. A milk-derived composition containing urea at a level of more than 0.2% of the total solids can be obtained by treating natural products such as milk or milk materials with an NF membrane or RO membrane to bring a fraction containing urea into the permeate side.

3 Claims, No Drawings

METHODS OF ISOLATING UREA, UREA COMPOSITIONS AND METHODS FOR PRODUCING THE SAME

This application is a divisional of prior application Ser. No. 09/532,628, filed Mar. 22, 2000 now abandoned. The complete disclosure of this previous application is hereby incorporated by this reference thereto.

BACKGROUND OF THE INVENTION

1. Field of the Invention

The present invention relates to methods for readily isolating urea from a solution containing urea using membrane isolation technology. By using isolating methods of the present invention, urea can be readily isolated and recovered, for example, from natural products, and also urea can be readily isolated and removed from sewage.

Further, the present invention relates to compositions containing milk-derived urea and to methods for producing the same. The compositions containing milk-derived urea of the present invention can be readily isolated and recovered from milk or milk materials by using membrane isolating technology, and can be used as urea materials derived from natural products.

Isolation using membranes first started with the use of an RO membrane to convert seawater to freshwater. Until today, various membranes have been used in different fields. Use of membranes in a dairy industry started with the isolation of whey proteins from whey using an ultra filtration (UF) membrane. Today, all the membranes, i.e., an NF membrane, RO membrane, UF membrane, and microfiltration (MF) membrane are used.

2. Description of the Related Art

Urea, a compound expressed by a chemical formula $CO(NH_2)_2$, was discovered by F. M. Rouelle in 1773, and the first organic compound that was successfully synthesized by F. Wohler in 1828. Since then, various methods of synthesizing urea have been proposed. Today, urea is synthesized by the direct method using ammonia and carbon dioxide as starting materials. Urea thus obtained is manufactured on a large scale, and used as an industrial raw material for products, such as urea resins, or as raw materials for chemical fertilizers, medicines and the like.

Urea is a final nitrogenous decomposition product of amino acids, nucleic acid bases and the like, and found in the blood and body fluids of vertebrates, and the urine of mammals. Urea is also found in nematodes, arthropods, mollusks, mushrooms, molds and the like. It is known that urea is present in the muscle of mollusks, such as sharks, in an amount of more than 1%, and also in the human blood in an amount of 0.02 to 0.03%. Urea is used as a raw material in agricultural chemicals, chemically synthesized products, medicines and the like. Furthermore, urea is admixed into hand creams or skin care creams to provide a moisturizing effect, or used as an effective component in diuretics.

Until now, no method of readily isolating and recovering urea from natural products has been reported. Thus, urea derived from natural products is not effectively used, and only synthesized urea is used.

On the other hand, the level of urea present in sewage is publicly regulated along with ammonia. The concentrations of ammonia and urea in sewage have to be less than 100 ppm. Accordingly, improved sewage treatment is needed. Proposed methods for removing urea today are hydrolyzation of urea into ammonia and carbon dioxide, and reaction of urea with nitrifying bacteria. However, these methods involve extremely complicated steps, such as heating at a high temperature or the use of microorganisms. Thus, it is currently difficult to satisfy these standards for sewage. Accordingly, development of methods of readily isolating and recovering urea from natural products, or readily isolating and removing urea from sewage is in great need.

Furthermore, there is a need to produce urea-containing compositions derived from natural products, which can be used in manufacturing products, such as cosmetics and medicines, where safety is a concern.

SUMMARY OF THE INVENTION

The present inventors intensively studied the development of methods of readily isolating and recovering urea from natural products with the view of effectively utilizing urea of natural origin. As a result, the present inventors found that urea actually permeates a nanofiltration (NF) membrane and reverse osmotic (RO) membrane, which were said to be permeable only to water and salts. Thus, the present inventors found that urea can be brought into the permeate side by treating a urea-containing fraction extracted from natural products or sewage containing urea, with an NF membrane or RO membrane.

Furthermore, the present inventors found that a milk-derived composition containing urea at a level of more than 0.2% of the total solids can be obtained by treating natural products such as milk or milk materials with an NF membrane or RO membrane to bring a fraction containing urea into the permeate side. The present inventors then found that the milk-derived urea-containing composition can be used as a highly safe urea material of natural origin in manufacturing hand creams, diuretics and the like, and completed the present invention.

Accordingly, the present invention provides methods of readily isolating and recovering urea, which can be used as a raw material in cosmetics, medicines, fertilizers, and the like, from natural products, and methods of readily isolating and removing urea from sewage in the process of sewage treatment.

Furthermore, the present invention provides methods of producing a milk-derived urea-containing composition which can be used as a urea material of natural origin, by recovering the permeate by treating milk or milk materials with an NF membrane or RO membrane.

DETAILED DESCRIPTION OF THE PREFERRED EMBODIMENT

In the present invention, an NF membrane or RO membrane is used to isolate urea from solutions containing urea. Further, in the present invention, an NF membrane or RO membrane is used to produce compositions containing milk-derived urea. Unlike an ultrafiltration (UF) membrane or microfiltration (MF) membrane, an NF membrane or RO membrane used in the present invention has no micro pores on the membrane surface. Thus, the mechanism for the permeability of an NF membrane or RO membrane has not been revealed, and it is today difficult to theoretically explain why urea, which has been known not to permeate an NF membrane or RO membrane, can permeate these membranes. One theory is the intramembrane dissolution and dispersion theory that certain substances dissolve and disperse within a membrane while permeating. This intramembrane dissolution and dispersion theory may well explain why urea permeates an NF membrane or RO membrane. Namely, urea is considered to readily dissolve in an NF membrane or RO membrane.

Examples of RO membranes to be used in the present invention include Dasal-3 Desalination), HR-95 (Dow Danmark), and NTR-729HF (Nitto Denko). Examples of NF membranes include Desal-5 (Desalination), NF-45 (Dow Danmark), and NTR-7450(Nitto Denko). The shape of membranes to be used is not restricted, and can be selected depending on the solutions to be treated. If sanitary conditions are required, a spiral membrane is desirable. If solutions to be treated are highly viscous or contain large particles, a hollow fiber membrane is not suitable, and a spiral membrane is appropriately used.

A treatment temperature between 5 C. and 60 C. is desirable for treatment of solutions containing urea with an NF membrane or RO membrane. Urea could be decomposed at a temperature higher than 60 C. Treatment efficiency decreases at a temperature below 5 C. Other conditions such as the pressure and flow rate for the treatment can be the same as those ordinarily used in NF membrane or RO membrane treatment.

Thus, solutions containing urea can be treated with an NF membrane or RO membrane to bring the urea into the permeate side for isolation, then the isolated urea can be recovered or removed as required.

Further, in the present invention, milk or milk materials are treated with an NF membrane or RO membrane to bring urea-containing compositions into the permeate side, then these milk-derived urea-containing compositions are recovered, and, if necessary, concentrated or dried by ordinary methods. If the salt concentration of solutions containing urea is high, the salt concentration of the permeate also becomes high. Therefore, it is desirable to lower the salt concentration of the urea-containing solutions by desalting before the treatment, or by desalting the resultant urea-containing solutions. Such desalting can be done using ion-exchange resins or an electrodialysis (ED) membrane. Thus, urea-containing compositions, which are derived from natural products are highly safe, and which can be used for producing hand creams, diuretics and the like, can be readily isolated and recovered from milk or milk materials. The urea compositions thus isolated and recovered characteristically produce no ammonia or the like since they contain no urea decomposing enzyme, and make highly safe and readily usable urea materials.

Milk or milk materials can be treated with an NF membrane or RO membrane at a permeable solid concentration. However, it is better to treat at lower solid concentrations of milk or milk materials to obtain compositions having a high urea concentration, although the filtrating efficiency may decrease.

The following test examples will explain the permeation of urea through an NF membrane or RO membrane.

In the following test examples, quantitative measurements were carried out by the urease indole method for urea and by the ash method for minerals.

Test Example 1

A solution containing 0.5% urea, 1% sodium chloride and 1% soybean proteins (model solution) was prepared. This model solution (5 kg) was subjected to a dialysis filtration with the addition of 5 volumes of water using an NF membrane having a salt suppression ratio of 50% (Desal-5, a product of Desalination). The membrane treatment was carried out at an operation temperature of 15 C. and at a pressure of 1.2 Mpa. The solution which permeated through this NF membrane into the permeate side was recovered, and concentrated with an evaporator. The resulting concentrate was desalted with cation exchange resins (IR-120B, a product of Organo), then anion exchange resins (IRA-410, a product of Organo).

The amount of urea contained in the resulting desalted concentrate was measured to be 24 g. It was revealed that urea can be isolated and recovered at a yield of 98% from the model solution, since 5 kg of the model solution contained 25 g of urea.

The amount of minerals contained in the desalted concentrate was below the measurable limit.

Test Example 2

A model solution containing 0.5% urea, 1% sodium chloride and 1% soybean proteins was prepared as described in Test Example 1. This model solution (5 kg) was subjected to a dialysis filtration with the addition of 5 volumes of water using an RO membrane having a salt suppression ratio of 95% (NTR-7450, a product of Nitto Denko). The membrane treatment was carried out at an operation temperature of 15 C. and at a pressure of 1.8 Mpa. The solution which permeated through this RO membrane into the permeate side was recovered, and concentrated with an evaporator.

The amount of urea contained in the resulting desalted concentrate was measured to be 19 g. It was revealed that urea can be isolated and recovered at a yield of 76% from the model solution, since 5 kg of the model solution contained 25 g of urea.

The amount of minerals contained in the desalted concentrate was 3 g.

In the following examples, quantitative measurements were carried out by the urease indole method for urea and by the ash method for minerals, as described in the test examples.

EXAMPLE 1

Skim milk containing urea at a concentration of 11.6 mg/100 ml was concentrated 2 times using an RO membrane having a salt suppression ratio of 98% (Desal-3, a product of Desalination). The membrane treatment was carried out at an operation temperature of 50 C. and at a pressure of 1.8 Mpa. The solution which permeated through this RO membrane into the permeate side was isolated and recovered.

The urea concentration of the resulting solution was 10 mg/100 ml (urea recovery: 86.2%).

The mineral concentration of this solution was 12 mg/100 ml.

EXAMPLE 2

Sewage containing urea at a concentration of 1.1 mg/100 ml was subjected to a dialysis filtration with the addition of 3 volumes of water using an NF membrane having a salt suppression ratio of 50% (Desal-5, a product of Desalination). The membrane treatment was carried out at an operation temperature of 15 C. and at a pressure of 1.3 Mpa. The solution which permeated through this NF membrane into the permeate side was isolated, and recovered.

The urea concentration of the resulting solution was 0.98 mg/100 ml (urea recovery: 89.0%).

EXAMPLE 3

Skim milk (50 L) containing urea at a concentration of 11.0 mg/100 ml was concentrated 2.5 times using an NF membrane having a salt suppression ratio of 50% (Desal-5, a product of Desalination). The membrane treatment was carried out at an operation temperature of 50 C. and at a pressure of 1.3 Mpa. The resultant permeate isolated and recovered from this NF membrane treatment was freeze-dried to obtain 50 g of powder of a milk-derived urea-containing composition.

The composition of this powder of a milk-derived urea-containing composition is shown in Table 1. The urea concentration was 6.2%.

TABLE 1

| Water | 3.0 (%) |
|---|---|
| Fat | 0.2 |
| Protein | 25.3 |
| Carbohydrate | 3.1 |
| Minerals | 68.4 |

EXAMPLE 4

Cheese whey containing urea at a concentration of 8.7 mg/100 ml was concentrated 2 times using an RO membrane having a salt suppression ratio of 98% (Desal-3, a product of Desalination). The membrane treatment was carried out at an operation temperature of 50 C. and at a pressure of 1.8 Mpa. The resultant permeate isolated and recovered from this RO membrane treatment was concentrated with an evaporator. The resulting concentrate was desalted with cation exchange resins (IR-120B, a product of Organo), then anion exchange resins (IRA-410, a product of Organo), and freeze-dried to obtain 5.5 g of powder of a mil-derived urea-containing composition.

The urea concentration of this powder of a milk-derived urea-containing composition was 81%.

POSSIBLE USE IN INDUSTRY

Solutions containing urea, such as urea-containing natural products or fractions containing urea extracted from natural products, or sewage containing urea, can be treated with an NF membrane or RO membrane to isolate urea in the permeate side, then the isolated urea can be recovered, and if necessary, purified, concentrated or dried by ordinary methods. If the salt concentration of solutions containing urea is high, the salt concentration of the permeate also becomes high. Therefore, it is desirable to lower the salt concentration of the urea-containing solutions by desalting before the treatment, or by desalting the resultant urea-containing solutions. Such desalting can be done using ion-exchange resins or an electrodialysis (ED) membrane. Thus, urea which can be used as a raw material for chemically synthesized products, medicines, fertilizers and the like can be readily isolated and recovered from natural products. The urea compositions thus isolated and recovered characteristically produce no ammonia or the like since they contain no urea decomposing enzyme, such as urease, and are accordingly very useful. For the removal or urea, urea can be removed without further treatment. In the present invention, urea contained in sewage can be readily isolated and removed using an NF membrane or RO membrane.

Furthermore, according to the methods of isolating urea using an NF membrane or RO membrane of the present invention, urea can be readily isolated and recovered from urea-containing natural products or fractions containing urea extracted from natural products. Urea thus obtained can be used as a raw material for chemically synthesized products, medicines, fertilizers or the like.

Further, in the present invention, milk or milk materials are treated with an NF membrane or RO membrane, and the permeate is isolated and recovered to obtain milk-derived urea-containing compositions. The resulting milk-derived urea-containing compositions can be used as a urea material of natural origin for products which require safeness, such as hand creams and diuretics.

What is claimed is:

1. A method of isolating urea comprising the steps of:

contacting a solution containing urea with a nanofiltration (NF) membrane or reverse osmotic (RO) membrane, said solution being selected from a natural product containing urea, a fraction containing urea extracted from a natural product, or sewage containing urea;

dissolving and dispersing the urea in the membrane at a temperature of 5–60° C. under a pressure in a range including 1.2 MPa and 1.8 MPa;

bringing the urea into the permeate side; and recovering the urea-from the permeate.

2. A method as claimed in claim 1 wherein said solution containing urea is milk or a milk material.

3. A method of producing an urea-containing composition from a milk or milk product, comprising the steps of:

contacting a milk or milk product containing urea with a nanofiltration (NF) or reverse osmotic (RO) membrane;

dissolving and dispersing the urea in the membrane;

bringing the urea into the permeate side; and recovering the permeate to obtain a composition containing milk-derived urea at a concentration of 0.2% or more of the total solid of the composition.

* * * * *